(12) United States Patent
Adams (10) Patent No.: US 7,002,098 B2
(45) Date of Patent: Feb. 21, 2006

(54) METHOD OF MAKING A NEEDLE AND A NEEDLE

(75) Inventor: Chad Michael Adams, West Jordan, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 105 days.

(21) Appl. No.: 10/732,025

(22) Filed: Dec. 10, 2003

(65) Prior Publication Data

US 2004/0118902 A1 Jun. 24, 2004

Related U.S. Application Data

(63) Continuation of application No. 10/137,464, filed on May 1, 2002.

(51) Int. Cl.
*B23K 26/00* (2006.01)

(52) U.S. Cl. ............................. 219/121.6; 219/121.64
(58) Field of Classification Search ............. 219/121.6, 219/121.63, 121.64, 121.85
See application file for complete search history.

(56) References Cited

U.S. PATENT DOCUMENTS

| | | | |
|---|---|---|---|
| 4,100,393 A | * | 7/1978 | Luther .................... 219/121.71 |
| 4,166,457 A | | 9/1979 | Jacobsen et al. ............. 128/639 |
| 4,280,496 A | | 7/1981 | Van Baelen ............. 128/214 R |
| 4,846,811 A | | 7/1989 | Vanderhoof ................ 604/263 |
| 4,883,468 A | | 11/1989 | Kousai et al. .............. 604/164 |

(Continued)

FOREIGN PATENT DOCUMENTS

| | | |
|---|---|---|
| DE | 28 25 346 A1 | 12/1979 |
| DE | 212 423 | 8/1984 |
| EP | 1 250 943 A1 | 10/2002 |
| WO | WO 99/08742 | 2/1999 |
| WO | WO 01/68174 A2 | 9/2001 |

OTHER PUBLICATIONS

PCT International Search Report.

*Primary Examiner*—M. Alexandra Elve
(74) *Attorney, Agent, or Firm*—Mony R. Ghose (57) ABSTRACT

A method is provided for forming a feature on a needle. In particular, a hollow, metal cannula has a first end, a second end and a substantially constant outer diameter extending over at least a portion of its length. An annular metal sleeve is provided that has a proximal shoulder and a distal shoulder. The length of the annular sleeve is less than the length of the constant diameter portion of the cannula. The sleeve has an inner diameter approximately equal to or less than the outer diameter of the constant diameter portion of the cannula. Two edges extend axially along the length of the sleeve, from the proximal shoulder to the distal shoulder, thereby defining a slit. The sleeve is positioned on the cannula at the constant outer diameter portion in an interference fit. An additional mechanical junction may be provided to secure the sleeve to the cannula. For example, the sleeve may be welded to the cannula using a laser welder at at least one edge of the sleeve near one of either the proximal face or the distal face. Alternatively and additionally, the sleeve may be crimped or glued to the cannula. In accord with another aspect of this invention, a needle is provided made in accord with this method.

18 Claims, 8 Drawing Sheets

U.S. PATENT DOCUMENTS

| | | | | |
|---|---|---|---|---|
| 5,215,528 A | | 6/1993 | Purdy | 604/164 |
| RE34,416 E | * | 10/1993 | Lemieux | 604/164.08 |
| 5,364,373 A | | 11/1994 | Waskonig et al. | 604/272 |
| 5,372,582 A | * | 12/1994 | Skrabal et al. | 604/44 |
| 5,419,766 A | | 5/1995 | Chang et al. | 604/110 |
| 5,540,667 A | | 7/1996 | Tanner, II | 604/192 |
| 5,556,410 A | | 9/1996 | Mittermeir et al. | 606/185 |
| 5,558,651 A | | 9/1996 | Crawford et al. | 604/263 |
| 5,601,536 A | * | 2/1997 | Crawford et al. | 604/263 |
| 5,647,849 A | | 7/1997 | Kalin | 604/111 |
| 5,683,365 A | | 11/1997 | Brown et al. | 604/110 |
| 5,702,367 A | * | 12/1997 | Cover et al. | 604/110 |
| 5,704,926 A | | 1/1998 | Sutton | 604/282 |
| 5,897,508 A | | 4/1999 | Konrad | 600/573 |
| 5,954,670 A | | 9/1999 | Baker | 600/567 |
| 6,012,213 A | * | 1/2000 | Chang et al. | 29/447 |
| 6,117,108 A | | 9/2000 | Woehr et al. | 604/110 |
| 6,183,440 B1 | | 2/2001 | Bell | 604/110 |
| 6,322,537 B1 | | 11/2001 | Chang | 604/164 |
| 6,379,333 B1 | | 4/2002 | Brimhall et al. | 604/164 |
| 2002/0026154 A1 | | 2/2002 | Chang | 604/198 |
| 2002/0103463 A1 | | 8/2002 | Luther et al. | 604/263 |

* cited by examiner

METHOD OF MAKING A NEEDLE AND A NEEDLE

This application is a continuation of application Ser. No. 10/137,464 filed May 1, 2002.

FIELD OF THE INVENTION

The subject invention relates to the field of infusion therapy. In particular, the invention is related to an introducer needle having a shoulder disposed at a predetermined distance from the tip of the needle and to a method for making such a needle.

BACKGROUND OF THE INVENTION

Catheters, particularly intravenous (IV) catheters, are used for infusing fluid, such as normal saline solution, various medicaments and total parenteral nutrition, into a patient or withdrawing blood from a patient. Peripheral IV catheters tend to be relatively short, and are on the order of about one and one-half inches in length. The most common type of IV catheter is an over-the-needle peripheral IV catheter. As its name implies, an over-the-needle catheter is mounted over an introducer needle having a sharp distal tip. The catheter and the introducer needle are assembled so that the distal tip of the introducer needle extends beyond the distal tip of the catheter with the bevel of the needle facing up away from the patient's skin.

The catheter and introducer needle assembly is inserted at a shallow angle through the patient's skin into a peripheral blood vessel, i.e., a smaller blood vessel that is not connected directly to the heart but is one of the branches of the central blood vessels that is directly connected to the heart. In order to verify proper placement of the assembly in the blood vessel, the clinician confirms that there is flashback of blood in the needle and in a flashback chamber located at the proximal end of the needle, which is typically formed as part of the needle hub. Once proper placement is confirmed, the clinician applies pressure to the blood vessel by pressing down on the patient's skin over the distal tip of the introducer needle and the catheter. This finger pressure occludes further blood flow through the introducer needle. The clinician withdraws the introducer needle, leaving the catheter in place, and attaches a fluid-handling device to the catheter hub. Once the introducer needle is withdrawn from the catheter, it is a "blood contaminated sharp" and must be properly handled.

In recent years, there has been great concern over the contamination of clinicians with a patient's blood and a recognition that "blood contaminated sharps" must be immediately disposed. This concern has arisen because of the advent of currently incurable and fatal diseases, such as Acquired Immunosuppressive Deficiency Syndrome ("AIDS"), which can be transmitted by the exchange of body fluids from an infected person to another person. Thus, contact with the body fluid of an HIV-infected person should be avoided. As noted above, if an introducer needle has been used to place a catheter in the vein of an HIV-infected person, the introducer needle may be a vehicle for the transmission of the disease. Although clinicians are aware of the need to properly handle "blood contaminated sharps," in certain medical environments, such as emergency situations or as a result of inattention or neglect, needle sticks from contaminated introducer needles may occur.

As a result of the problem of accidental needle sticks by "blood contaminated sharps," various needle shields have been developed. Examples of such shields are disclosed in U.S. Pat. No. 6,004,294 and U.S. patent application Ser. No. 09/717,148 (filed Nov. 21, 2000), both incorporated herein by reference. These shields operate by engaging a feature, such as an enlarged diameter portion, formed on the needle. The engaging means may take many forms, such as a spring gate biased to contact the enlarged diameter portion of the needle when the tip of the needle is within the shield. Due to the small size of the needle and its delicate structure, it has been difficult to provide a feature that can withstand adequate force without affecting the operation of the needle itself. Further, such features have traditionally included a ramp, a radius or angled surface extending from the surface of the needle that may create difficulty in capturing the tip within the shield or may result in exertion of force on the needle in a non-axial direction.

SUMMARY OF THE INVENTION

It is therefore an advantage of one aspect of the instant invention to provide a needle and method of making a needle that may be employed with various safety-engineered shielding devices.

It is an advantage of another aspect of the invention to provide a needle and a method for making a needle having a feature with a right-angled shoulder.

It is an advantage of another aspect of the instant invention to provide a needle having a sleeve secured to a cannula at a predetermined location and a method for securing the sleeve to the cannula at the predetermined location.

It is an advantage of yet another aspect of the instant invention to provide a technique for securing a feature on a needle having a sharp, right angled shoulder that can be readily captured by an engaging means in a needle shield and, once captured, can direct the forces from the engaging means to the needle in a substantially axial direction.

In accord with one aspect of the invention, a method is provided for forming a feature on a needle. In particular, a hollow, metal cannula has a first end, a second end and a substantially constant outer diameter extending over at least a portion of its length. An annular metal sleeve is provided that has a proximal shoulder and a distal shoulder. The length of the annular sleeve is less than the length of the constant diameter portion of the cannula. The sleeve has an inner diameter approximately equal to or less than the outer diameter of the constant diameter portion of the cannula. Two edges extend axially along the length of the sleeve, from the proximal shoulder to the distal shoulder, thereby defining a slit. The sleeve is positioned on the cannula at the constant outer diameter portion in an interference fit. An additional mechanical junction may be provided to secure the sleeve to the cannula. For example, the sleeve may be welded to the cannula using a laser welder at at least one edge of the sleeve near one of either the proximal face or the distal face. Alternatively and additionally, the sleeve may be crimped or glued to the cannula. In accord with another aspect of this invention, a needle is provided that has been made in accord with this method.

Certain implementations of this aspect of the invention provide that the proximal shoulder is perpendicular to the axis of the cannula or the distal shoulder is perpendicular to the axis of the cannula. The sleeve may be welded to the cannula proximate to both the proximal face and the distal face, or a seam weld may be applied along the length of the sleeve. Alternatively or additionally, the sleeve may be crimped or glued to the cannula. The sleeve may be formed by rolling a flat metal sheet into an annular shape, such as a cylinder, and then slipped onto the cannula. A window may be formed in the sleeve at a predetermined position with respect to the slit and the sleeve may be welded to the cannula at the window. Such a window may be disposed in the sleeve at a position 180 degrees from the slit.

In accord with another aspect of the invention, a distinct mechanical junction is formed between the sleeve and the cannula to secure the feature in place. For example, a notch is formed in the outer surface of the cannula at a predetermined position along the length of the cannula. A cylindrical sleeve has an inner cavity with an inner diameter that is less than the outer diameter of the outer surface of the cannula. The sleeve is positioned over the cannula such that the notch is disposed within the inner cavity. The sleeve is crimped such that at least a portion of the sleeve is deformed radially inward, causing the sleeve to engage the notch. Certain implementations of this aspect of the invention provide that the sleeve is welded to the cannula after crimping or that an adhesive is employed to join the sleeve to the cannula. The use of an adhesive may be particularly advantageous to hold the sleeve in place before the crimp or weld is formed.

In accord with yet another aspect of the invention, a needle includes a hollow, metal cannula having a first end, a second end, a beveled tip at the second end, an axis, a cannula length extending from the first end to the second end, and an outer diameter. A distinct annular metal sleeve is fixedly attached to the cannula at a predetermined position with respect to the tip. The sleeve has a proximal shoulder and a distal shoulder, and a sleeve length extending from the proximal shoulder to the distal shoulder. At least one of the proximal shoulder or the distal shoulder is perpendicular to the axis of the cannula. Certain implementations of this aspect of the invention provide that the sleeve has two edges extending axially along the sleeve length from the proximal shoulder to the distal shoulder, thereby defining a slit and a weld is disposed along the slit. A flash opening may be positioned in the cannula, proximal to the sleeve, that would provide the caregiver with a visual indication when the beveled tip of the needle has accessed the patient's vein. Radially extending tabs may be positioned on the sleeve to orient the needle during manufacture and use.

DETAILED DESCRIPTION

Figure 4:
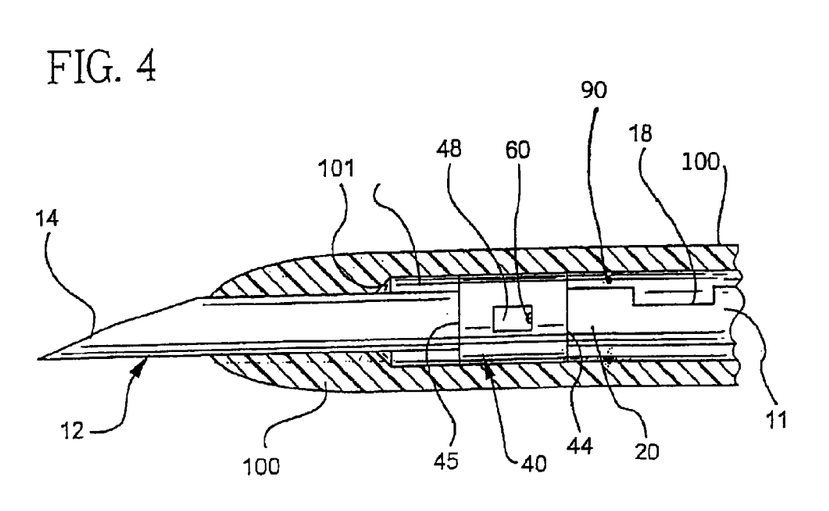
FIG. 4 is a cut-away side view of the cannula and catheter of FIG. 3.

As used herein, the term "proximal" refers to a location on the needle 1 that, during normal use, is closest to the clinician using the device and farthest from the patient in connection with whom the device is used (the right side of FIG. 4). Conversely, the term "distal" refers to a location on the needle that, during normal use, is farthest from the clinician using the device and closest to the patient in connection with whom the device is used (the left side in FIG. 4).

In various stages of the manufacture of needle assemblies and during the use of needles, it would be advantageous to have a distinct feature on the needle 1 that is secured at a fixed location and orientation with respect to the rest of the needle 1, particularly the tip 14. For example, such a feature may be employed to orient the needle 1 with respect to a needle hub or holder. Consequently, the needle tip 14 would also be at a fixed orientation with respect to the holder. A caregiver would thus know immediately to orientation of the needle tip 14 by simply grasping the holder. Further, such a feature may be more readily graspable by machines designed to automatically manufacture needles and over-the-needle catheter assemblies. The feature may be used to engage a ledge 101 in a catheter 100 (see FIG. 4), thereby positioning the needle at a particular location within the catheter and ensuring that the tip 14 of the needle extends out of the catheter a satisfactory distance. Additionally, such a feature may be more readily grasped by a safety device designed to capture the needle tip 14 after use.

In accord with an aspect of the invention, a needle 1 includes a cannula 10 having a ferrule or sleeve 40 attached at a fixed, predetermined position along the length of the cannula. As will be discussed more fully below, the sleeve 40 is preferably sized with an inner diameter that is smaller than the outer diameter of the cannula. Consequently, there is an interference fit between the sleeve 40 and the cannula which helps maintain the sleeve in its predetermined position. Additional mechanical junctions or bonds 60 may be provided to better maintain the sleeve 40 in place. With the sleeve 40 in place, the needle 1 includes a feature (which may include the proximal shoulder 44 and/or distal shoulder 45 of the sleeve, or the sleeve itself, or some other structure attached to or formed integral with the sleeve, such as a tab 80) that can be employed for various purposes related to the manufacture and use of the needle 1. For example, once formed, the needle 1 may be inserted into a catheter 100 for insertion into the tissue of a patient. After use, the needle 1 may be withdrawn from the catheter. The needle tip 14 may then be captured within a safety-engineered shielding device that grips the feature such as disclosed in U.S. Pat. No. 6,004,294 and U.S. patent application Ser. No. 09/717,148, incorporated herein by reference.

The cannula 10 includes a proximal end 11 and a distal end 12 extending along an axis 13. Typically, the cannula has a cylindrical shape. Preferably, at least a portion 21 of the cannula has a constant outer diameter. A beveled tip 14 is positioned at the distal end of the cannula. The beveled tip may be formed of two beveled surfaces, a proximal bevel 15 and a distal bevel 16 (see FIG. 2), that are disposed at different angles from the axis of the cannula to ease entry into a patient's vein. The cannula includes an outer surface 20 and an inner surface 19. The inner surface 19 defines a central cavity 17 that extends from the proximal end of the cannula to the distal end, forming a tip opening 23 at the distal end.

A flash opening 18 is located in the wall of the cannula 10, creating a fluid flow path from the central cavity 17 to the exterior of the cannula within the catheter 100. Preferably, the flash opening is proximal to the sleeve 40. The catheter is operably engaged to a flash chamber 90. The flash chamber may simply be the annular space about the needle within the catheter (see FIG. 4) or a separate chamber located in a needle hub. During use, this flow path provides the caregiver with a visual indication that the vein has been successfully entered because a small amount of blood will flow through the tip opening, through the flash opening and into the flash chamber where it is visible to the caregiver. As shown in FIG. 4, the catheter is translucent so that blood in the annular space 90 is visible to the caregiver.

Figure 9:
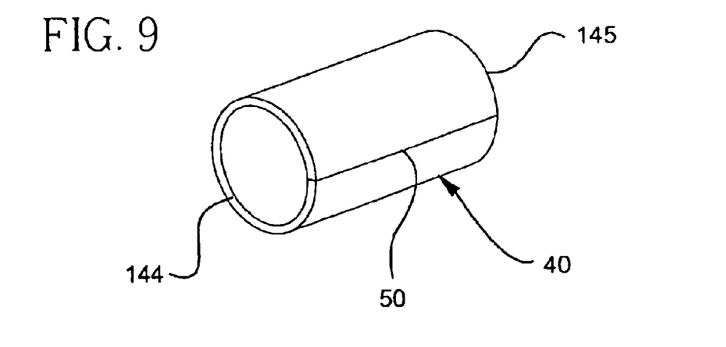
FIG. 9 is a perspective view of a sleeve in isolation.
Figure 10:
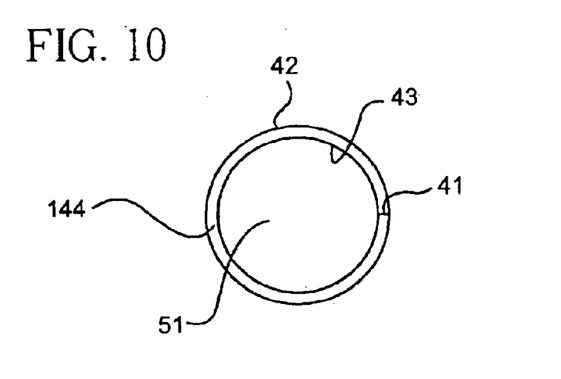
FIG. 10 is a front elevation view of the sleeve of FIG. 9.
Figure 11:
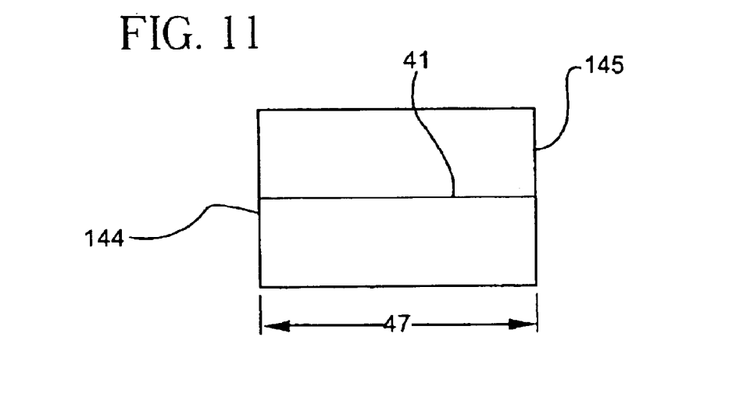
FIG. 11 is a side elevation view of the sleeve of FIG. 9.

The ferrule or sleeve 40 preferably has a substantially cylindrical shape (see FIG. 9) formed by an exterior surface 42, an interior surface 43, and a length 47 extending from a distal face 145 to a proximal face 144. The interior surface 43 defines an inner cavity 51. Importantly, in accord with certain implementations of the invention, the sleeve 40 is sized to tightly fit on the cannula in an interference fit. The length 47 of the sleeve 40 is preferably no longer than the length of the constant diameter portion 21 of the cannula. As can be seen in FIG. 4, when the sleeve 40 is positioned on the cannula, the distal face forms a distal shoulder 45 and the proximal face forms a proximal shoulder 44. Preferably, the distal shoulder and the proximal shoulder are perpendicular to the outer surface 20 of the cannula 10 and to the cannula axis 13.

Figure 5:
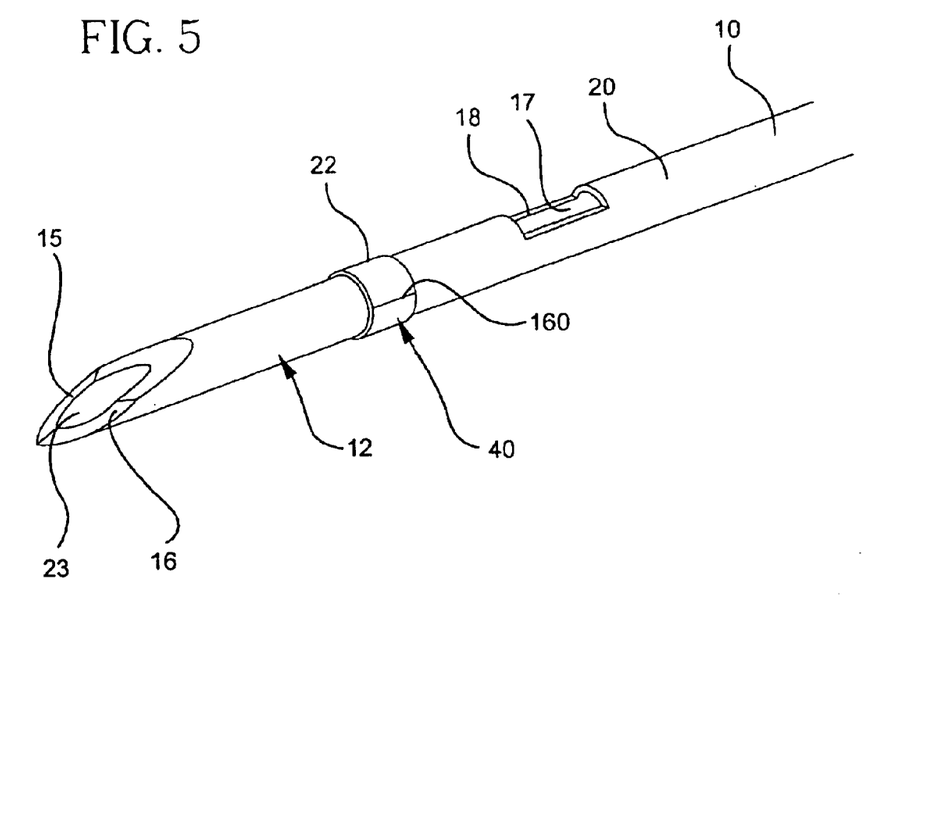
FIG. 5 is a perspective view of a cannula and a sleeve in accord with another aspect of the invention.
Figure 6:
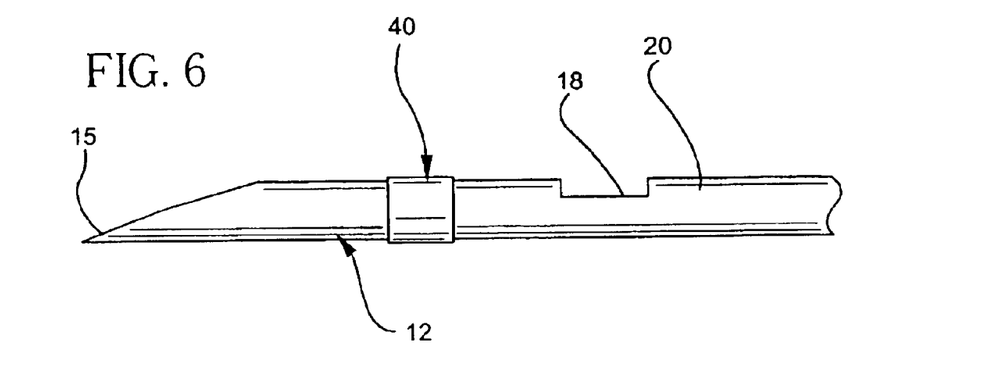
FIG. 6 is a side elevation view of the cannula and sleeve of FIG. 5.

A slit 50 is formed in the sleeve 40 and defined by two edges 41. Preferably, the slit extends axially through the sleeve 40 from the proximal face 144 to the distal face 145. The slit may also have other shapes and still practice the invention. In particular, the slit may proceed around the sleeve 40 in a spiral shape or other curved shapes. Before positioning the sleeve 40 on the cannula, the edges are adjacent or nearly adjacent (see FIG. 5). As the sleeve 40 is forced onto the cannula, the edges separate to accommodate the larger outer diameter of the cannula within the inner cavity 51.

Figure 12:
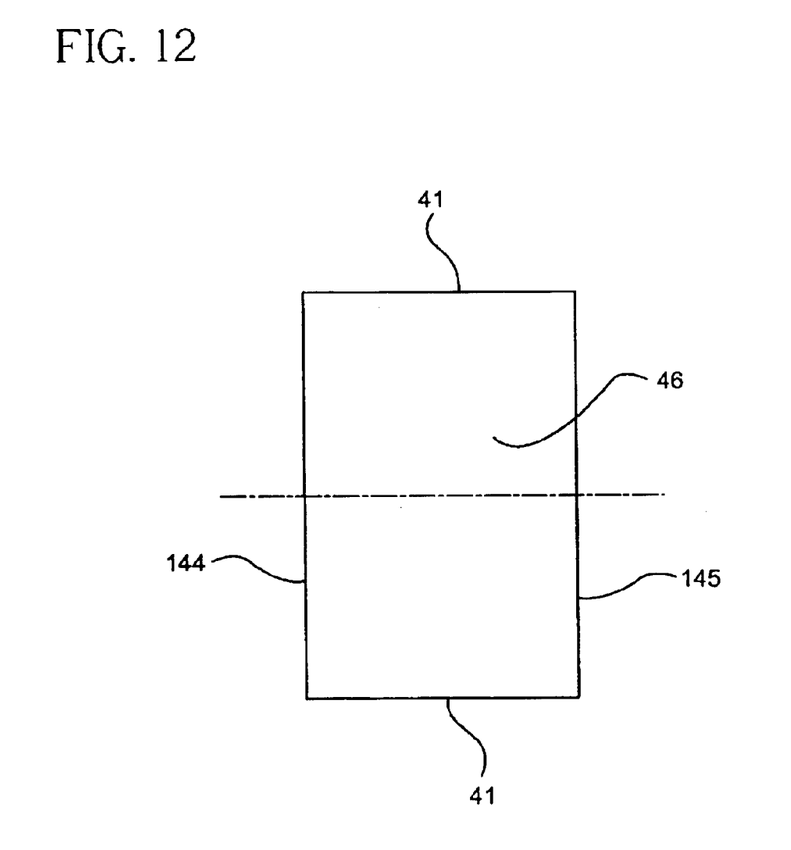
FIG. 12 is a top elevation view of a sheet used to form the sleeve of FIG. 9.

The sleeve 40 may be formed in any manner such as extruding, casting or the like. If the sleeve 40 is initially formed as a complete cylinder, the slit 50 can be formed in the sleeve, such as by cutting, burning and so on. In one implementation of the invention, the sleeve 40 is formed of a flat sheet 46 (see FIG. 12). The sheet is rolled into a nearly cylindrical shape, bringing the edges together and thereby forming the slit. The sheet is sized so that the slit extends over less than 180 degrees of arc along the diameter of the sleeve when the sleeve is positioned on the cannula. Preferably, the slit extends over 20 degrees of arc or less when the sleeve is positioned on the cannula. It will be appreciated that the slit may be larger or smaller and still practice the invention. Further, in certain implementations, the slit may be formed as a groove disposed in the sleeve 40 that does not extend fully through the sleeve 40 radially (that is, the edges are connected by a thin webbing before mounting the sleeve on the cannula).

Once the sleeve 40 is formed, it is slipped over the distal end 12 of the cannula 10 and positioned at a predetermined location on a constant diameter portion 21 of the cannula. Preferably, the sleeve 40 is located a distance from the tip 14 such that the tip and the sleeve may be secured within a shield after use, as discussed in U.S. Pat. No. 6,004,294, incorporated herein by reference, and U.S. application Ser. No. 09/717,148, incorporated herein by reference. It will be appreciated that the sleeve 40 may be located at other locations and still practice aspects of the invention. Further, the sleeve 40 may be formed in other manners and be positioned on the cannula in different ways and still practice aspects of the invention. For example, the flat sheet 46 may be rolled directly onto the cannula and secured in place as disclosed herein.

As discussed above, the diameter of the inner cavity 51 of the sleeve 40 is preferably less than the diameter of the outer surface 20 of the cannula 10, creating a close interference fit between the sleeve and the cannula. The edges 41 of the sleeve 40 are forced apart to accommodate the outer diameter of the cannula. If webbing connects the edges, it is broken as the cannula is forced into the inner cavity. In any event, there is preferably direct contact between the interior surface 43 of the sleeve 40 and the outer surface 20 of the cannula when the sleeve is positioned on the cannula.

Figure 1:
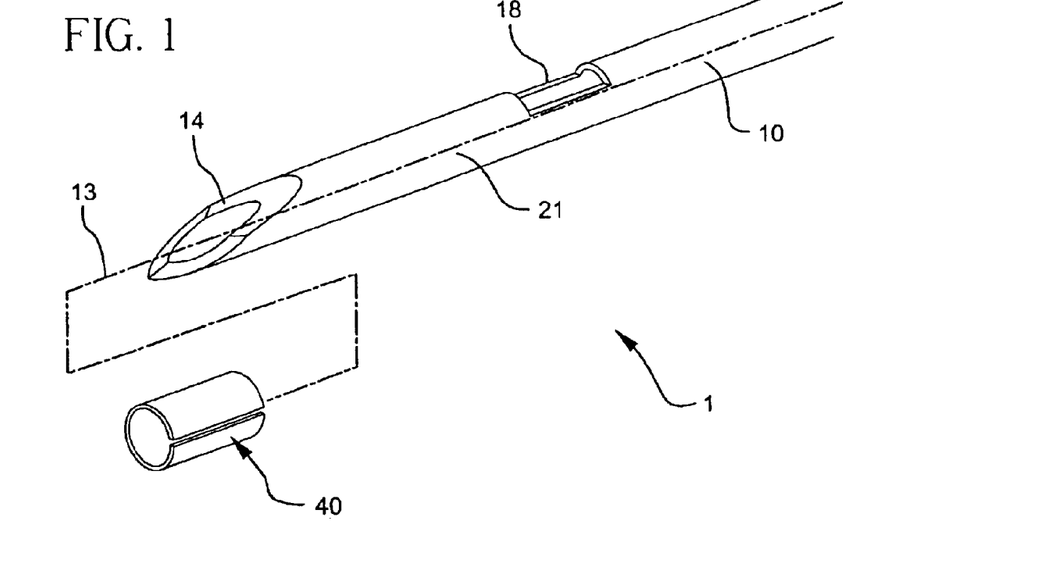
FIG. 1 is an exploded perspective view of a cannula and sleeve in accord with one aspect of the invention.
Figure 2:
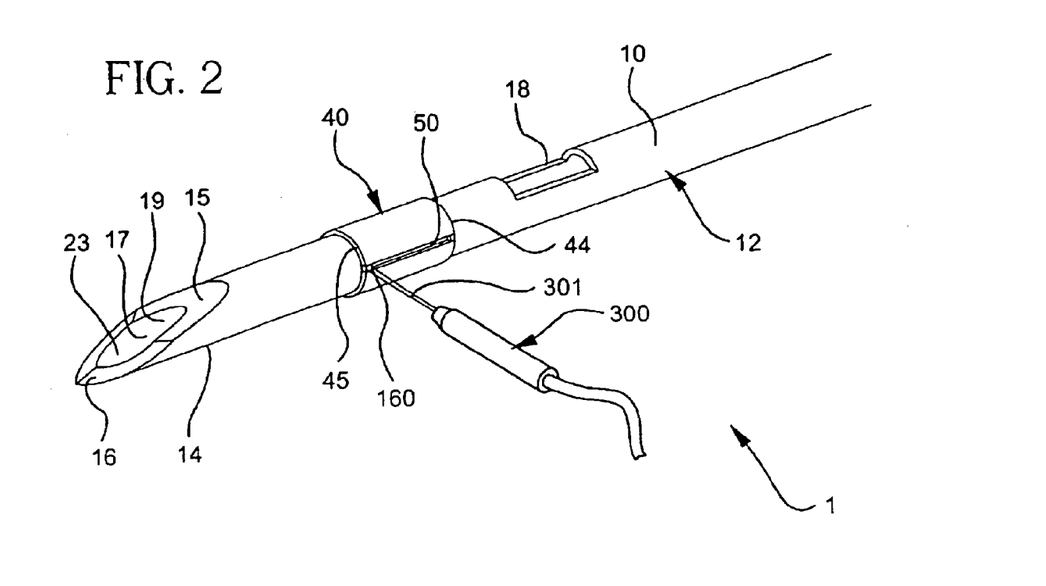
FIG. 2 is a perspective view of a cannula and sleeve in accord with an aspect of the invention with a seam weld.

The interference fit between the interior surface 43 of the sleeve 40 and the outer surface 20 of the cannula prevents movement of the sleeve 40 along the length of the cannula under certain loads. Indeed, the interference fit alone may provide adequate resistance to the movement of the sleeve 40 for a particular application such that the interference fit may be deemed an adequate mechanical junction. In certain circumstances, however, a greater resistive force will be desired. In those circumstances, an additional mechanical junction 60 is provided, securing the sleeve 40 to the cannula. For example, the sleeve 40 may be welded to the cannula using a laser welder. As depicted in FIG. 2, a laser beam 301 from a laser welding device 300, such as an Nd: Yag laser welder, model Luxstar LX50 may be directed at contact points on the sleeve 40. The sleeve and the cannula are in direct physical engagement at the contact points. A seam weld 160 may then be created along the slit 60 by delivering a laser beam in a series of spots over the length of the sleeve.

Figure 7:
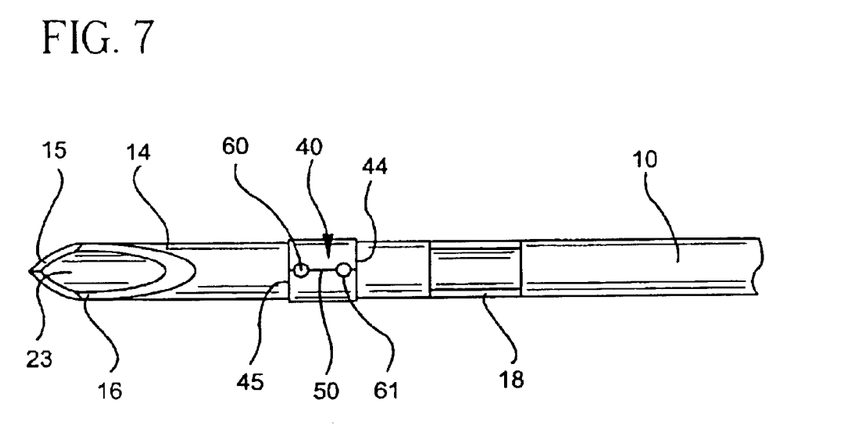
FIG. 7 is a top elevation view of a cannula and sleeve in accord with another aspect of the invention.
Figure 8:
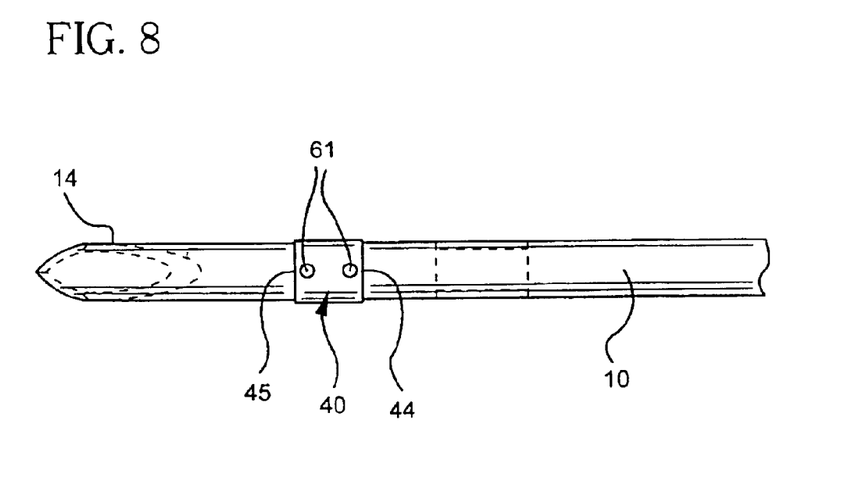
FIG. 8 is a bottom elevation view of the cannula and sleeve of FIG. 7.

Other techniques for welding may also be employed. Referring to FIGS. 7 and 8, two of the contact points or weld points 61 are positioned along the edges 41 at the slit 50, one near the proximal shoulder 44 and one near the distal shoulder 45. The laser beam is directed at the juncture of the edge and the cannula at the slit. The laser melts the material of the sleeve 40 and the cannula, which, in turn, cools to form a weld, integral with both the sleeve 40 and the cannula, securing them together. Two other contact points or weld points 64 are disposed on the opposite side of the sleeve 40, 180 degrees from the slit. Again, these weld points are disposed near the proximal shoulder 44 and the distal shoulder 45. The laser beam is directed at the exterior surface 42 of the sleeve 40, melting through the wall of the sleeve so that the beams melt at least some portion of the outer surface 20 of the cannula 10. The melted portions of the sleeve 40 and the cannula 10 cool to form a weld, integral with both the sleeve and the cannula, securing them together.

Figure 3:
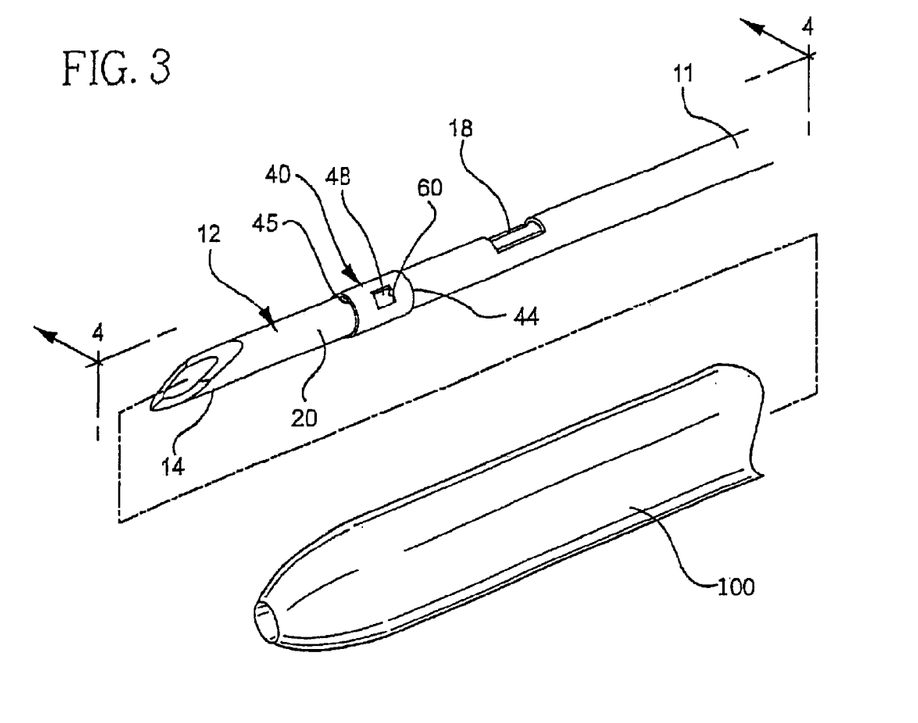
FIG. 3 is an exploded perspective view of a cannula and an over-the-needle catheter in accord with an aspect of the invention.

These four welds may be created by splitting a single laser beam into four beams, and applying them to the desired weld points for a controlled period of time, depending on the dimension of and materials forming the sleeve 40 and the cannula 10, as well as the desired resistive force to be withstood by the mechanical junction 60. It will be appreciated that other techniques for welding, in particular other techniques for laser welding, may be employed and still practice aspects of the invention. For example, the weld may be provided at locations distinct from the slit. Currently, on one preferred application of the invention, two seam welds 160 are formed disposed 180° from each other, neither being located along the slit. The laser beam is delivered to the surface of the sleeve and creates a weld, bonding the sleeve to the cannula along both seams. Alternatively or additionally, a window 48 may be provided in the sleeve. The mechanical junction 60 can be formed by a spot weld at the edge of the window (see FIGS. 3 and 4).

The dimensions and materials of the sleeve 40 and cannula 10, as well as the operation of the laser welder, will depend on the particular application for the needle 1. It is preferred that the sleeve 40 and the cannula be formed of a similar alloy to ensure that a satisfactory mechanical bond is formed by the laser weld or other mechanical junction. In one application of the instant invention, the cannula is made of fully hard 301 (or 302) stainless steel and has an outer diameter of between 0.007 and 0.080 inch (including, around 0.055 inch). The sleeve 40 is formed from a sheet of fully hard 301 (or 302) stainless steel about 0.002 inch thick and about 0.050 inch long. The weld points are preferably about 0.005 inch inward from the proximal and distal shoulders. Most preferably, the sleeve 40 contacts the cannula where the weld is applied. In any event, it is preferred that there be a gap of no more than 0.0010 inches at a desired weld point. The laser beam is applied to the weld points for a period of 0.2 seconds at 100 Hz at a setting of 30–50 KW. The resulting weld at the weld point is about 0.010 inch in diameter and can withstand an axial force of about 30–50 lbs.

Figure 13:
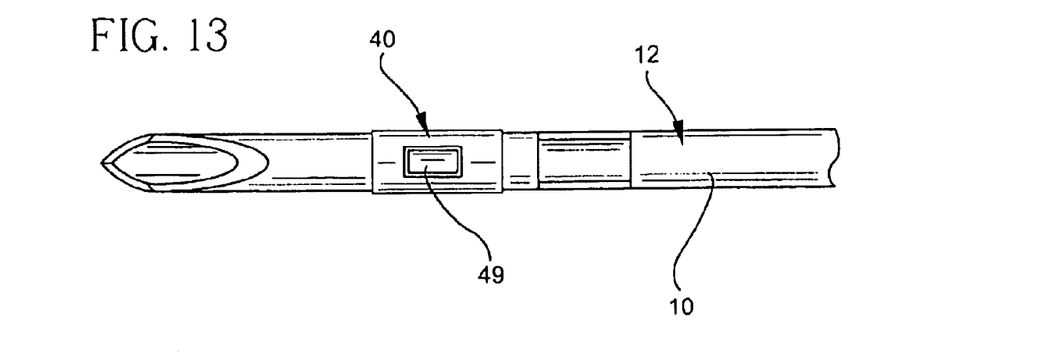
FIG. 13 is a top elevation view of a cannula and sleeve in accord with an aspect of the invention.
Figure 14:
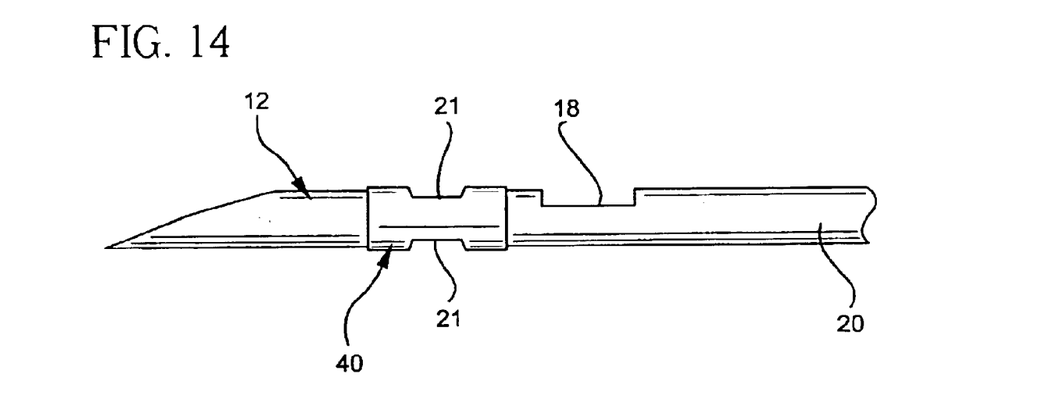
FIG. 14 is a side elevation view of the cannula and sleeve of FIG. 13.
Figure 15:
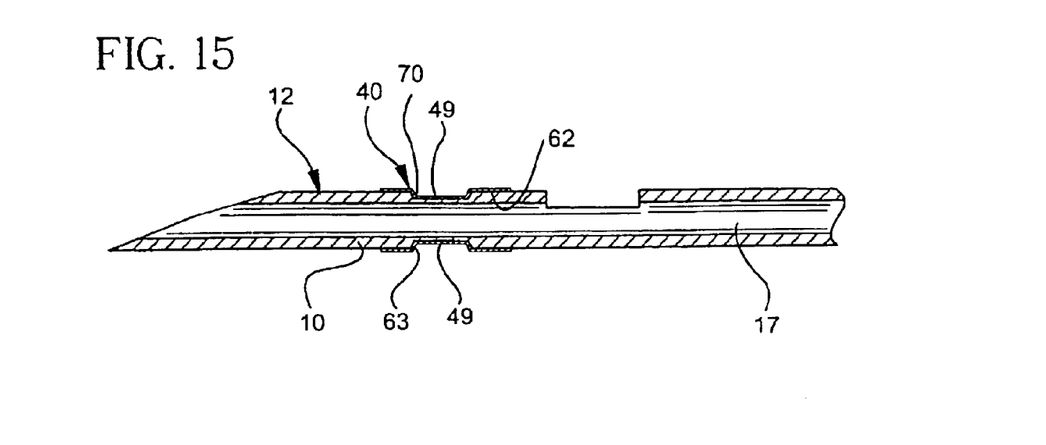
FIG. 15 is a cut-away side view of the cannula and sleeve of FIG. 13.

Referring to FIGS. 13–15, another form of mechanical junction may be employed in connection with an aspect of the instant invention. Crimp notches 70 are formed in the cannula at a desired location, such as at the otherwise constant diameter portion 21 of the cannula (constant, that is, excluding the crimp notches). Preferably, the crimp notches do not penetrate the wall of the cannula. However, the crimp notches 70 may be formed as cut outs in the cannula wall. Further, the flash notch 18 may be employed as a crimp notch. The number, location and shape of the crimp notches 70 may be selected based on the particular application of the needle. For example, two crimp notches may be employed, disposed on opposite sides of the cannula at a position distal to the flash notch 18 (see FIG. 15). The sleeve 40 is formed and slipped over the cannula until it is disposed directly over the crimp notches, capturing the crimp notches within the inner cavity 51. The sleeve 40 is then crimped into the crimp notches 21, creating a mechanical engagement at junction 63 between the sleeve and the cannula. The sleeve 40 may also be secured to the cannula using an adhesive material 62 or weld points 61. The use of an adhesive material may be particularly advantageous to maintain the sleeve in position on the cannula until crimping or welding is completed.

Figure 16:
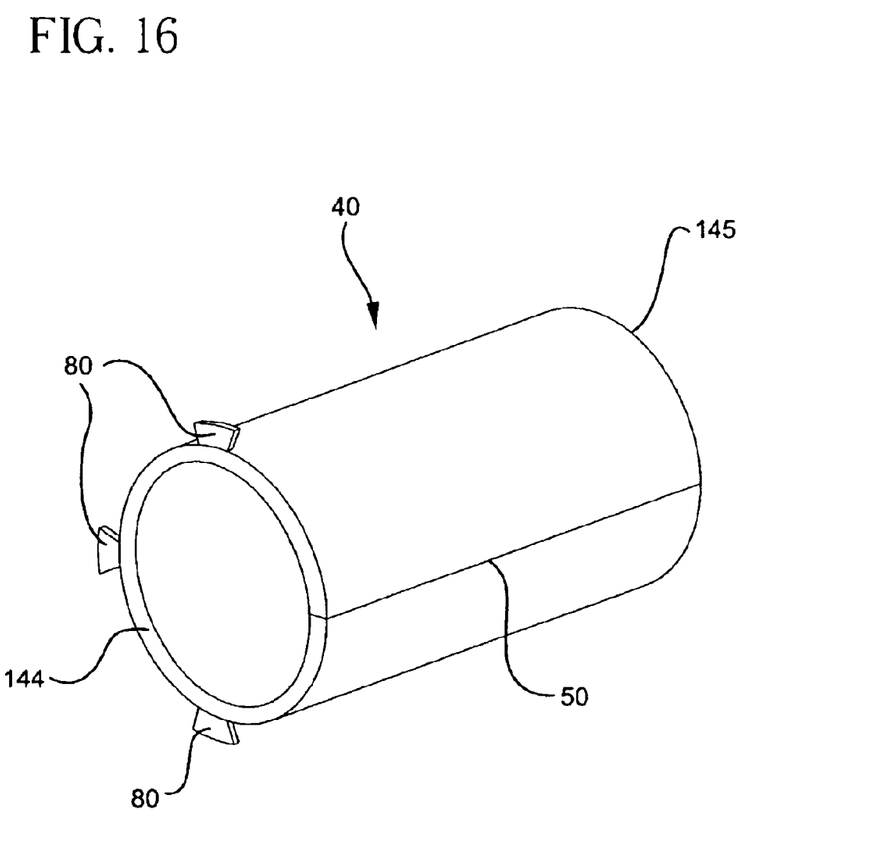
FIG. 16 is a perspective view of a sleeve for use in accord with aspects of the invention.

As discussed above, the feature on the needle 1, such as the sleeve 40 and/or its proximal and distal shoulders, are preferably symmetric about the axis of the catheter. It will be appreciated that the sleeve 40 may have other distinct shapes and still practice the invention. For example, tabs or ribs 80 (see FIG. 16) may be formed on the sleeve 40 that extend radially outward or which extend axially from the distal shoulder or the proximal shoulder along the surface of the cannula. Such tabs or ribs may be employed to orient the cannula (and thus the needle tip 14) with the catheter 100 (and thus a hub that is grasped by a caregiver). Further, such tabs or ribs may be used as a register to observe and control the orientation of the cannula during the manufacturing process. The tabs or ribs may also be designed to cooperate with various structures in a needle shield to better capture the needle tip 14.

Further, as disclosed herein, the cannula has a substantially cylindrical shape. It will be appreciated that the cannula may have other shapes and still practice aspects of the invention. For example, the cannula may have an oval cross section such that the sleeve 40 contacts the cannula only along the major axis of the oval. Conversely, the sleeve may be formed with an inner cavity having an oval cross section such that it contacts the outer surface 20 of the cannula at the minor axis of the oval. The mechanical junction may then be formed at those contact points, such as by welding, using an adhesive material 62 or crimping the sleeve 40 into a notch on the cannula.

It is preferred that the sleeve 40 actually contacts the cannula at the weld point during welding. Such a contact is preferably achieved by the interference fit between the sleeve 40 and the cannula. However, it will be appreciated that the sleeve 40 may be sized such that there is no interference fit and practice aspects of the invention. For example, a solder material may be disposed about the cannula as the sleeve 40 is slipped into position before welding. Advantageously, a solder that also functions as an adhesive material may be employed. If the internal diameter of the sleeve 40 is larger than the outer diameter of the cannula, there will be a space between the cannula and the sleeve that might interfere with satisfactory laser welding. To overcome this difficulty in this situation, the sleeve 40 may be biased in a direction against the outer surface 20 of the cannula to achieve a contact point where welding can take place. Further, other welding techniques may not require the close positioning of the sleeve 40 and the cannula to achieve a satisfactory weld. In fact, in certain circumstances, the sleeve 40 may be sufficiently thick that enough material can be melted by the laser welder to effect an adequate weld without affecting the integrity of the sleeve.

As discussed herein, four spot weld points or two seam welds are employed. Any number of welds and weld points may be employed as is required to achieve a satisfactory bond between the sleeve and the cannula for a given application. Further, the weld points and seams may be located at other positions and still practice aspects of the invention. For example, the sleeve 40 may be secured to the cannula with a single weld formed in the sleeve at any position, such as a position remote from the slit. The weld point may be at the juncture of the proximal shoulder and/or the distal shoulder and the outer surface 20 of the cannula. The weld may be a single contiguous line extending axially along the full length of the sleeve 40, or circumferentially about a diameter of the sleeve.

The sleeve 40 is preferably positioned along the cannula at a point distal of the flash notch 18. It will be appreciated that the sleeve may be positioned at other locations and still practice aspects of the invention. For example, the flash notch 18 may be positioned between the sleeve 40 and the tip of the cannula. Alternatively, the sleeve 40 may be positioned in engagement with or partially covering the flash notch 18. Further, the slit may be orientated at different locations with respect to the flash notch 18 and practice aspects of the invention.

The proximal shoulder and the distal shoulder preferably form right-angled surfaces with the outer surface 20 of the cannula. It will be appreciated that the shoulders may have different shapes and still practice aspects of the invention. For example, the shoulder may be provided with an undercut at the cannula surface, creating a crevice that may engage certain types of grasping mechanisms contained within shields Further, the proximal face 144 and distal face 145 may have curved or notched surfaces, depending on the particular application of the invention.

Although the invention is described herein in connection with a needle 1 employed with a peripheral IV catheter and a safety shield, it is understood that the invention is applicable to other needles, such as hypodermic needles, epidural needles and so forth. In addition, while this invention is satisfied by embodiments in many different forms, preferred embodiments of the invention are shown in the drawings and described in detail herein. The scope of the invention is measured by the appended claims.

We claim:

1. A method of making a cannula having a feature comprising:

providing a cannula having a first end, a second end, a length and an outer surface with en outer diameter;

forming a notch in the outer surface of the cannula at a predetermined position along the length of the cannula;

providing a sleeve with a cylindrical shape and an inner cavity defining an inner diameter that is less than the outer diameter of the outer surface of the cannula, wherein the sleeve has a slit, wherein the slit extends over 20 degrees of arc or less when positioned on the cannula;

positioning the sleeve over the cannula such that the notch is disposed, at least in part, within the inner cavity; and crimping the sleeve such that at least a portion of the sleeve is deformed radially inward, causing the sleeve to engage the notch.

2. The method of claim 1 further comprising welding the sleeve to the cannula after crimping.

3. A cannula formed by the method of claim 1.

4. A method of forming a needle comprising:

providing a hollow, metal cannula having a first end, a second end, a beveled tip at the second end, an axis, a cannula length extending from the first end to the second end, and an outer diameter;

providing a distinct annular metal sleeve positioned on the cannula at a predetermined position with respect to the tip, the sleeve having a proximal shoulder and a distal shoulder, and a sleeve length extending from the proximal shoulder to the distal shoulder, wherein a slit is disposed in the sleeve, wherein the slit extends over 20 degrees of arc or less when positioned on the cannula; and forming a mechanical bond integrally with the sleeve or the cannula, thereby fixedly attaching the sleeve to the cannula at a predetermined location.

5. The method of claim 4 wherein the mechanical bond includes a crimp formed in the sleeve engaging a notch in the cannula.

6. The needle of claim 4 wherein the mechanical bond is a weld.

7. A needle formed by the method of claim 4.

8. A method of forming a feature on a cannula comprising:

providing a hollow, metal cannula having a first end, a second end, an axis, a length extending from the first end to the second end, and an outer surface extending over at least a first portion of the length;

providing an annular sleeve with an exterior surface, wherein the sleeve has a slit extending over 20 degrees of arc or less when positioned on the cannula;

positioning the sleeve on the cannula at the first portion of the cannula; and joining the sleeve to the cannula by welding through the sleeve to the cannula.

9. The method of claim 8 further comprising delivering a laser beam to an exterior surface of the sleeve and welding through the sleeve to the cannula.

10. The method of claim 8 wherein a contact point between the sleeve and the cannula exists before joining occurs.

11. The method of claim 8 wherein a rib is mounted to the sleeve, extending, at least in part, radially outward from the exterior surface of the sleeve.

12. The method of claim 8 further comprising providing a flat metal sheet and rolling the sheet into an annular shape to form the sleeve.

13. The method of claim 8 further comprising positioning an adhesive material between the sleeve and the cannula, securing the sleeve to the cannula.

14. A method of forming a feature on a cannula comprising:

providing a cannula having a first end, a second end, an axis, a length extending from the first end to the second end, and an outer diameter extending over at least a first portion of the length;

providing a sleeve with a proximal shoulder, a distal shoulder, an inner diameter, a sleeve length extending from the proximal shoulder to the distal shoulder, and a slit extending over 20 degrees of arc or less when positioned on the cannula;

positioning the sleeve on the cannula at the first portion of the cannula in an interference fit such that the sleeve accommodates the cannula; and welding the sleeve to the cannula.

15. The method of claim 14 further comprising crimping the sleeve to the cannula.

16. The method of claim 14 wherein welding comprises providing a seam weld formed by a laser welder extending substantially the full length of the sleeve.

17. The method of claim 14 wherein the sleeve is glued to the cannula by an adhesive material before welding.

18. A cannula formed by the method set forth in claim 13.

* * * * *